United States Patent [19]
Langberg

[11] 4,456,374
[45] Jun. 26, 1984

[54] DETECTING THE PRESENCE OR ABSENCE OF A COATING ON A SUBSTRATE

[75] Inventor: Edwin Langberg, Marlton, N.J.

[73] Assignee: Johnson & Johnson, New Brunswick, N.J.

[21] Appl. No.: 329,793

[22] Filed: Dec. 11, 1981

[51] Int. Cl.³ .................... G01N 21/88; G01N 21/89
[52] U.S. Cl. .................................. 356/237; 250/572; 356/430
[58] Field of Search ............... 356/237, 239, 429, 430, 356/431; 250/562, 563, 572

[56] References Cited

U.S. PATENT DOCUMENTS 3,460,893  8/1969  Wilks, Jr. .......................... 356/300
4,297,032  10/1981  Temple .............................. 356/239

FOREIGN PATENT DOCUMENTS 55-85209  6/1980  Japan ................................. 356/237
898828  6/1962  United Kingdom ............... 356/239

Primary Examiner—Vincent P. McGraw
Attorney, Agent, or Firm—Jason Lipow

[57] ABSTRACT

A method and apparatus is provided for determining the presence or absence of a coating on a substrate. The substrate is placed into optical contact with a light guide and the principle of frustrated total internal reflection is utilized. Light scattered from the coating surface is monitored to indicate the presence of a coating and failure to detect scattered light indicates the absence of said coating.

25 Claims, 4 Drawing Figures

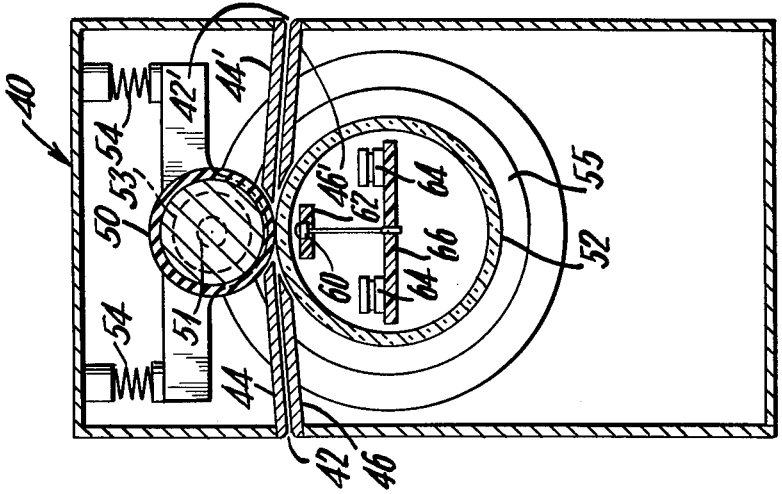
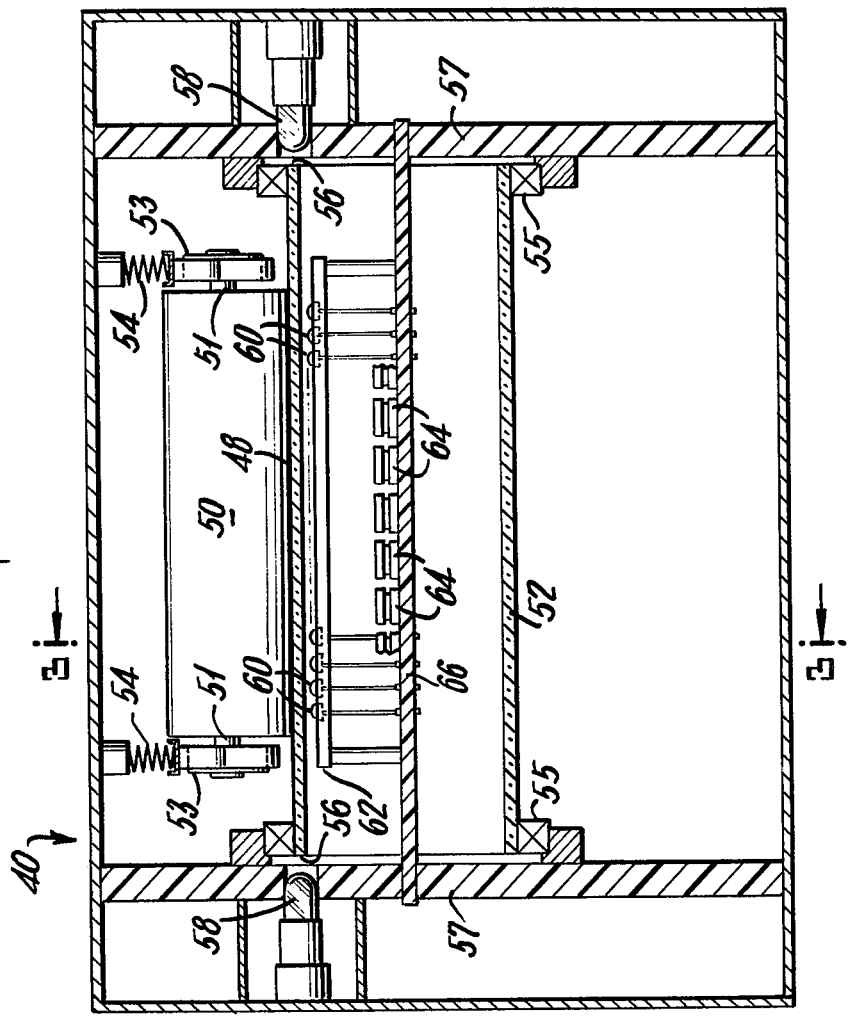

DETECTING THE PRESENCE OR ABSENCE OF A COATING ON A SUBSTRATE

BACKGROUND OF THE INVENTION

This invention relates to method and apparatus for detecting the presence or absence of a coating on the surface of a substrate. In particular this invention is directed toward evaluating the efficiency of coating processes on sheet-like materials such as paper, cloth, polymer films or the like, utilizing the principles of frustrated total internal light reflection.

The phenomenon of total internal light reflection has been long known in the field of optics. Concisely stated, this phenomenon is the observation that when a beam of light is directed onto a first end surface of a longitudinally extending medium having a relatively high refractive index and surrounded by a second medium having a relatively low refractive index, the light does not pass through the longitudinal interface between the medium but instead is reflected back into the first medium. Ultimately, through successive total internal reflections, the light passes through the first medium along its longitudinal length and out the end remote from the first end. Said in other words, the light is trapped essentially totally, within the first medium and does not escape from first medium along its longitudinal interface. It is also known that in the process of total internal reflection, some associated electromagnetic field does escape the interface in the form of an evanescent, nonpropagating field, normal to the medium interface, the aplitude of which decays rapidly into the second medium, at an exponential decay rate with the distance from the interface. This principle is described and applied in "Internal Reflection Spectroscopy", N. J. Harwick, Harwick Scientific Corporation, Ossing, New York (1979).

In the above referenced publication, the principle of frustrated total internal reflection has been suggested for employment in various applications such as, for example, an inkless finger printing apparatus.

SUMMARY OF THE INVENTION

It has now been discovered that the phenomenon of frustrated total internal reflection may be employed to determine and monitor the presence or absence of a thin coating on a sheet material such as paper, film, cloth or the like. It has been discovered that such method, and apparatus for carrying out the method, may be utilized essentially independently of the reflective properties of the coating or the substrate to which it is applied.

In accordance with the method of this invention, the surface of the substrate carrying the coating to be monitored is placed in optical contact with a light guide. As used herein the term "light guide" is meant to denote a medium having the property of essentially total internal reflection. Said in other words, such light guide will comprise a medium which extends in a longitudinal direction bounded by first and second end surfaces and longitudinal interfaces with the surrounding medium. When a beam of light is directed onto the first end surface of such light guide such that the beam of light will strike the longitudinal interface between the light guide and its surrounding medium obliquely, the light will then be essentially totally reflected back into the light guide, at an angle of reflection essentially equal to the angle of incidence with the longitudinally interface. In accordance with accepted theory, some electromagnetic field escapes the light guide at the point of incidence at the longitudinal interface. This escaped field is in the form of an evanescent, nonpropogating wave, normal to the medium interface which field decays rapidly in amplitude as an exponential function of the distance from the interface.

The degree to which the reflection of light energy back into the light guide approaches totality is, among other factors a function of the relative values of the refractive index of the light guide medium as compared to the refractive index of the medium surrounding the longitudinal interface. For example, a glass rod having a high refractive index relative to that of surrounding air will exhibit a high degree of total internal reflection. On the other hand, by pressing a surrounding medium such as for example, coated paper against the glass rod, the total light reflection is frustrated and light can leak to the surrounding medium where it is scattered, transmitted or absorbed. As used herein, the term "optical contact" is meant to denote the bringing together of a medium of a given refractive index such as for example the coated surface of a substrate, and a light guide surface into such intimate contact as to measurably affect the degree of total internal reflection of the light guide as contrasted with the degree of total internal reflection exhibited by the light guide in contact with a medium of lower reflective index e.g., air with a refractive index of unity.

In accordance with the method of this invention, a coated surface is brought into optical contact with a light guide and the amount of light leaked from the light guide and scattered in the contacting medium is measured. Any gaps in the coating along the longitudinal length of the interface between the light guide and the coated surface will result in a lesser amount of light leak from the light guide in the gap portion as contrasted with the coated portion and hence the gap will be detectable.

An apparatus is also provided for carrying out the method of this invention and comprises a light guide having a longitudinal interface and first and second end surfaces. A light source is provided for directing a beam of light onto the first end surface. Means are provided for bringing a coated substrate into optical contact with the longitudinal interface of the light guide and light leak detecting means are provided for measuring the light leaked from the longitudinal interface to the coated substrate and scattered, transmitted or absorbed.

In a specific embodiment, a plurality of light leak detecting means are provided along the longitudinal interface whereby coated and uncoated areas may be monitored by the relative quantity of light detected by the light leak detecting means. More specifically, the light detecting means may comprise photo detectors such as photodiodes which are capable of generating an electrical signal proportional to the light intensity detected. Such signal may be amplified and utilized to operate a device for signaling the presence or absence of a gap in the coating.

BRIEF DESCRIPTION OF THE DRAWINGS

FIG. 2 is a longitudinal cross-sectional view of an apparatus for carrying out the teachings of the invention.

FIG. 3 is a transverse cross-sectional view of the apparatus of FIG. 2;

DETAILED DESCRIPTION OF THE INVENTION

Figure 1:
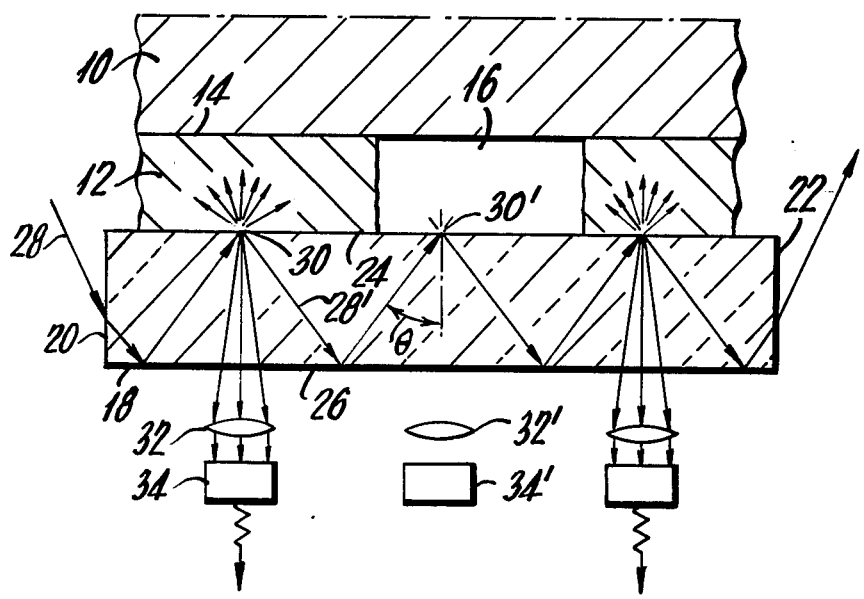
FIG. 1 is a schematic representation illustrating the method of this invention for detecting the presence or absence of a coating on a substitute.

Referring now to FIG. 1 of the drawings, illustrated there is a highly schematic greatly enlarged longitudinal cross-sectional view of a system for utilizing the method of this invention to detect gaps in a coating on a substrate. The substrate 10 may be, for example, any kind of sheet material to which a coating is to be applied, either in specific areas such as spots, lines, patches or the like or even across the full width of the sheet material. Such substrates may include for example, paper, cloth, or film to which such coatings as oil sprays, cohesives, adhesives, laminations of various kinds, or the like, are applied. For simplicity, coating 12, illustrated in FIG. 1, is chosen to be one which is intended to be uniformly applied to the surface 14 of substrate 10 although it will be understood that the teaching of this invention are readily applicable to monitoring coatings intended to be applied in various predetermined patterns.

The object of the system illustrated in FIG. 1 is to detect the presence of gaps, such as gap 16, in coating 12. To this end, the coated substrate 10 is placed into optical contact with a light guide 18. The light guide 18 is a longitudinally extending, light transmitting element, which may comprise glass, quartz, sapphire, or other suitable material and has a first end surface 20, a second end surface 22 and longitudinal interfaces 24 and 26, i.e., the interfaces between the light guide and the surrounding medium or media. It should be understood that while for exemplary purposes, the light guide is illustrated as being elongated in a longitudinal direction, the teachings of this invention is not limited to any particular geometric configuration and instead, such configuration is best chosen to suit the particular application of the methods described herein. For the purpose of monitoring coatings across the width of a web or sheet, the configuration illustrated in FIG. 1 is believed to be suitable.

The light guide 18 is chosen to be an element which has the property of essentially total internal light reflection when a beam of light such as beam 28 is directed onto the first end surface 20 so that it strikes the interface 24 at point 30' at an angle $\theta$, which is greater than the critical angle $\theta_c$. Under these circumstances the light beam is reflected from longitudinal interface to longitudinal interface in a zig-zag path and finally out the opposite second end surface 22. Essentially all the light energy is transmitted in this manner. The critical angle for a given system can be easily determined by calibration. The theory hypothesized as governing the phenomenon of internal light reflection is described in an article entitled, "Application of Internal Reflective Spectroscopy to the Study of Absorbed Layers at Interfaces" authored by H. R. Mark, Jr. and E. N. Randall and presented in Symposia of the Faraday Society, No. 4, 1970, a publication of The Faraday Society, London, England. In accordance with this theory the angle $\theta_c$ is equal to the function $\sin^{-1}(n_1/n_2)$, wherein $n_2$ is the refractive index of the light guide medium and $n_1$ is the refractive index of the medium at the longitudinal interface with the light guide. The theory also prescribes that for internal reflection, $n_2$ must be greater than $n_1$.

In accordance with the teachings of this invention the coating 12 of the substrate 10 is brought into optical contact with the longitudinal interface 24 of the optical guide 18 and a beam of light 28 is directed against end surface 20.

To assure optical contact, the contacting medium must have a refractive index greater than unity and preferably equal to that of the light guide which is typically greater than 1.2, e.g., 1.5. Secondly, the contacting medium must maintain an extended intimate contact with the longitudinal surface of the light guide so that the distance between the two surfaces must be less than 0.1 micrometer i.e., approximately 1/7th of the wavelength of light. There are only two ways of maintaining such intimate contact with the hard surface of the light guide. One is the precision optical grinding of another hard surface. The other is a contact with a material which has some "give" due to flow. It is the latter case which is used for detection of coatings. For example, an uncoated paper pressed against glass does not form an optical contact regardless of the refractive index of paper, in that the surface of paper, on the microscale of optical wavelengths, is so rough that only an occasional point contact is made with a glass light guide. On the other hand, paper coated with adhesive or cohesive coatings form optical contact because of the combined effect of bonding forces between the coating and the glass and the flow of the coating material which smoothes the roughness of the paper. It is believed that measurable contrast in leaked light between coated and uncoated paper can be detected when the coated area makes optical contact for at least 20% along its longitudinal interface with the light guide, i.e., at least 4% of the coated area is within a distance of 0.1 micrometers from the light guide.

It is therefore important to be sure that the coated substrate is in intimate contact with the light guide. The degree of contact may be controlled by applying pressure to the sample being monitored and the degree of pressure can easily be determined by calibration. In practice, it has been found useful to apply pressures in the range of from about 1.0 to about 20 pounds per square inch for a cohesive coating.

Referring again to FIG. 1, because of the optical contact between the coating and the light guide at a point of incidence, e.g. at point of incidence 30, the phenomenon of total internal reflection is destroyed and a small quantity of light energy leaks across the interface. Such leaked light is absorbed, transmitted and/or scattered by the coating or the substrate 10 to various degrees depending on the optical characteristics of the coated substrate.

Means are provided for measuring the leaked light energy. It should be understood that in its simplest embodiment, the light leak detecting means can comprise merely means for viewing the leaked light by the human eye. As is illustrated in FIG. 1 such means measure the portion of the leaked light that is scattered from the interface 24 or substrate 10, back through the light guide 18, and out through the opposite longitudinal interface 26. In the embodiment of FIG. 1, the means provided for measuring the scattered light leaked through interface 26 comprise a lens 32 which focuses such scattered light upon a photodetecting device such as a photodiode 34. The photodiode, in turn, produces an electrical signal proportional to the scattered light energy.

To detect gaps in the coating, a plurality of leaked light measuring means, such as lens 32 and diode 34, are provided along the longitudinal path of the light guide. Where a gap in the coating exists, optical contact is not made and the internally reflected component 28' of the light beam 28 does not substantially leak from interface 24 at a point of incident 30' with the interface but is instead essentially totally reflected back into the light guide at an angle essentially equal to that of its angle of incidence with interface 24. Accordingly, the escaped light measuring means, lens 32' and diode 34' does not detect any substantial light and does not generate any substantial electrical signal.

The contrast between light detected by the light leak detecting means, lens 32 and 34 as compared to light detected at lens 32' and 34' may be used to indicate the presence of the gap 16. More specifically the difference in electrical signals generated by the respective diodes may be used in conjunction with logic circuitry to signal the presence and/or location of gap 16.

As will be apparent to one skilled in the art from the teachings herein, the resolution of the system, i.e., the minimum gap width detectable, will be a function of the numbers of, and the spacings between, light leak detecting means and such design parameters may be chosen bearing in mind such factors as the resolution required for a particular application and the cost of providing a sufficient number of light detecting means.

The logic circuitry associated with the output of the light leak detecting means may be varied in accordance with the particular application. For example, in the simple system illustrated in FIG. 1, the circuitry may be designed to simply report or signal the existence of any gap in the coating within the measured width of the substrate. Alternatively, the circuitry may be designed to report or signal not only the existence of a gap but its specific location as well. Further still the circuitry may be designed to signal an "error" where gaps in certain locations occur but to "accept" the detection of gaps in other areas. Such a system is useful for example in providing control of a process for coating a substrate in a predetermined pattern. It should be clear that any of the above possible logic circuits may be used in combination, all dependant upon the desired application of the methods taught herein.

It will be understood that the method described herein can be utilized by measuring the leaked light transmitted, scattered or even absorbed by the coated substrate. For example, if the coated substrate is sufficiently transparent, the light leak detecting means could be provided and positioned above the substrate and measure transmitted light. Alternatively, if the coating were fluorescent, the light leak detecting means could simply comprise means for detecting a color change which would be indicative of absorbed light. The method chosen in the example illustrated by FIG. 1 is to measure leaked light from the interfacial surfaces which is sufficiently scattered by the coated substrate. This method has some particular advantages. For example if transmitted light were to be measured, the method would not be applicable to a substrate having printing on the surface opposite the coating as such printing could interfere with the transmission of light. This problem is totally obviated by measuring scattered light.

Referring now to FIGS. 2 and 3, illustrated therein is an apparatus for carrying out the method of this invention as described schematically in FIG. 1. The coated substrate (not shown) enters the apparatus 40 through entrance slot 42 between entrance guide plates 44 and 46 and leaves via exit slot 42' between exit guide plates 44' and 46'. In the course of its travel through apparatus 40, the substrate passes through the nip 48 between pressure roller 50 and light guide 52. The pressure roller 50 may comprise any suitable material, such as for example, a rubber roller, for exerting pressure on the substrate and forcing the coating into optical contact with the light guide 52. To this end, pressure exerting means such as springs 54 are provided, biased so as to urge roller 50 against light guide 32. Preferably, the springs are adjustable so that the apparatus may be calibrated to bring suitable pressure to bear against the substrate.

The light guide 52 is in the form of a hollow, relatively thinwalled cylinder which is preferably made out of a material such as glass. The longitudinal surface serves as the longitudinal interface at the nip 48 and, accordingly, the substrate should be fed into the apparatus so that the coated side is in contact with the light guide at this interface.

Preferably both the light guide and the roller are free to rotate about their respective axes to avoid excessive friction between the coated substrate and the surface of the device at the nip 48 and to allow the substrate to be passed, continuously and smoothly through the device. To this end roller 50 is supported by roller shaft 51 which, in turn, is rotatably supported in roller bearings 53. Similarly, light guide 52 is rotatably supported by light guide bearings 55. It will be understood that for the device illustrated in FIGS. 2 and 3, it is contemplated that the substrate will be drawn through the device by means external thereto. Nevertheless, it is equally possible to provide means for driving either the roller or the light guide and thereby drawing the substrate through the device.

The end surfaces 56 of the light guide in the vicinity of the nip correspond to the first and second end surfaces 20, 22 illustrated schematically in FIG. 1. Accordingly, bulbs 58 are provided for directing light against the end surface 56. Preferably the light is screened (not shown) so that essentially only the end surfaces 56 are illuminated and the remaining interior of the device is dark.

A series of longitudinally spaced leaked light detectors 60 are provided directly below the illuminated portion of the glass cylindrical wall of light guide 52 and supported within the hollow cylinder by stationary support 62. Such escaped light detectors preferably comprise a lens for focusing leaked light onto a photodetector such as a photodiode which generates an electrical signal in proportion to the light energy received by the diode. The lens assures that each photodetector looks at only a relatively small area of the substrate-light guide interface thereby assuring high resolution and eliminating interference.

The electrical signal output of the photodetector is electrically connected to a series of amplifiers 64 supported on a stationary printed circuit board 66 wherein the signal is amplified and passed to logic circuitry (not shown) which may be designed, for example, for reporting and signaling the presence or absence of a gap in the coating on the substrate.

The device illustrated in FIGS. 2 and 3 has been employed, for example, to detect the presence of a gap in a coating on a continuous web of paper intended for packaging certain medical products. The packaging material is imprinted on the side opposite the coating with logo and other informational matter. The coating is a cohesive material used to seal the package and comprises a formulation of natural latex and certain styrene-butadiene copolymers. The web may have various widths such as 1.25, 1.5 and 4 inches and the device is provided with circuitry which may be preset to monitor those alternative widths. The paper has a basic weight of 21 lbs. per 3000 square feet and is coated with a weight of adhesive of from 2.75 to 4.75 lbs. per 3000 square feet. The web moves through the device at a maximum web speed of 300 ft/min.

The device employed utilizes a set of high intensity quartz-halogen lamps as a light source, each being equipped with a quartz lens, the bulbs manufactured by the General Electric corporation and sold by them as G.E. model #2604X. The photodetector utilized is manufactured by the General Senser corporation and sold by them as GS3020-3 phototransistor. The phototransistor is equipped with a small lens for focusing leaked light as described above. The device is provided with a total of 32 light detectors (lens and phototransistor combinations) at a spacing density of eight detectors per inch along a longitudinal path of four inches. The device is found to have a resolution of 0.125 inches and in practice may reliablely detect gaps having a width of 0.25 inches or more.

Figure 4:
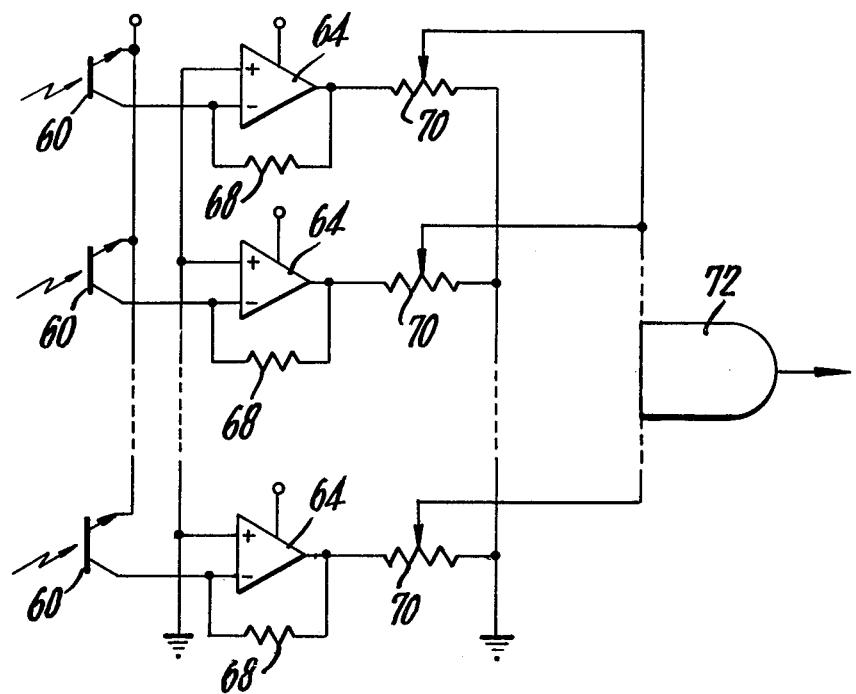
FIG. 4 is a circuit diagram of an electrical circuit monitoring and signaling gaps detected by the device of FIG. 2.

FIG. 4 is a simplified circuit diagram utilized in the device. The circuit includes thirty-two light detectors such as the phototransistors 60. The output of each phototransistors 60 is connected to the negative input terminal of an operational amplifier 64 ("OP AMP") whose gain is determined by feedback resistor 68. The positive input of each OP AMP 64 is connected to ground. The output of each of the thirty-two OP AMPS 64 is equalized by potentiometers 70, one of which is connected to the output of each OP AMP 64, to balance the system prior to feeding in a substrate. Each potentiometer 70 is also connected to and collectively operate a thirty-two input AND gate 72. In practice, the thirty-two input AND gate 72 comprises four interconnected 8-input AND gates such as Model No. CD 4048 manufactured by RCA.

In operation, leaked light energy is sensed by each of the phototransistors 60. The detected light energy causes a current flow resulting in a voltage differential at the input of the corresponding OP AMP 64. Normally, light energy will be detected at each phototransistor 60 representing the presence of a coating and resulting in a first output of the corresponding OP AMP 64 which, in turn, is coupled to the corresponding input to AND gate 72. When all phototransistors 60 detect the presence of a coating, the AND gate 72 has thirty-two voltage inputs above the threshold value for the gate. Whenever any one of the phototransistors 60 fails to detect the requisite quantity of light energy corresponding to the presence of a coating, the output of that phototransistor 60 will cause the output of its corresponding OP AMP 64 to yield a second output representing the absence of a coating which, in turn, will provide an input to the AND gate below its threshold value and hence invert the output of the AND gate 72. Thus, the detection of the absence of a coating by any phototransistor 60 will result in a change of the output of the AND gate 72 signifying a faulty condition.

What is claimed is:

1. A method for determining the presence or absence of a coating on at least a portion of a surface of a substrate comprising:

providing a light guide having end surfaces and a longitudinal surface therebetween;

placing said substrate on said light guide with the coated surface of the substrate in optical contact with the longitudinal surface of the light guide;

directing a beam of light at at least one of said ends of said light guide; and directly monitoring the light leaked through the interface of the light guide and the substrate.

2. The method of claim 1 wherein said beam is directed so that a component thereof is at an angle with the normal to the longitudinal surface of the light guide, said angle being sufficient to produce a measurable contrast between the light leaked at a coated area and the light leaked at a noncoated area.

3. The method of claim 2 wherein said angle is greater than the function $\sin^{-1}(n_1/n_2)$ wherein $n_2$ is the refractive index of the light guide and $n_1$ is the refractive index of a noncoated area.

4. The method of claim 1 wherein the coating has a refractive index greater than 1.0.

5. The method of claim 4 wherein the coating has a refractive index of about 1.5.

6. The method of claim 1 wherein the coating is in intimate contact with the longitudinal surface of the light guide.

7. The method of claim 6 wherein said coated surface is within 0.1 micrometers of said light guide longitudinal surface for at least 20% of the length of said interfaced surfaces.

8. The method of claim 1 wherein leaked light transmitted by said substrate is monitored.

9. The method of claim 1 wherein leaked light absorbed by said substrate is monitored.

10. The method of claim 1 wherein leaked light scattered from said substrate is monitored.

11. The method of claim 10 wherein leaked light from said substrate, scattered and transmitted through a longitudinal surface of the light guide, is monitored.

12. The method of claim 1 wherein the leaked light is monitered by eye.

13. The method of claim 1 wherein leaked light is measured by having said leaked light directed onto a photosensor which generates an electrical signal proportional to the intensity of said leaked light.

14. The method of claim 13 wherein said leaked light is directed onto said photosensor through a lens.

15. The method of claim 1 wherein said substrate is continuously passed over said light guide and leaked light is continuously monitored.

16. An apparatus for detecting the presence or absence of a coating on at least a portion of a surface of a substrate comprising:

a light guide having a longitudinal surface and first and second end surfaces;

a light source for directing a beam of light at the first end surface;

contacting means for placing said substrate on said light guide with the coated surface of the substrate in optical contact with the longitudinal surface of the light guide;

light leak detecting means for directly monitoring light intensity leaked through a longitudinal surface of said light guide from the interface of said substrate and said light guide.

17. The apparatus of claim 16 wherein the light guide has a refractive index greater than 1.2.

18. The apparatus of claim 16 wherein the light guide is glass.

19. The apparatus of claim 16 wherein the light guide is a hollow cylinder

20. The apparatus of claim 16 wherein said contacting means comprise pressure means for exerting pressure on said substrate.

21. The apparatus of claim 20 wherein said pressure means are adjustable whereby sufficient pressure may be aplied to the substrate to produce contrasting light leak between the coated and uncoated areas.

22. The apparatus of claim 21 wherein said pressure means comprise a rubber roller and an adjustable spring biased to apply adjustable pressure to said substrate.

23. The apparatus of claim 16 wherein said light detecting means comprise at least one photosensor positioned to intercept leaked light, said photosensor being capable of generating an electrical signal proportion to the intercepted leaked light.

24. The apparatus of claim 23 wherein said photosensor is positioned to detect leaked light scattered from said interface and transmitted through said light guide.

25. The apparatus of claim 24 wherein a plurality of photosensors are provided to detect leaked light, said plurality of photosensors being spaced along the interface of the light guide and the substrate.

* * * * *